(12) United States Patent
Liu et al.

(10) Patent No.: US 10,188,596 B2
(45) Date of Patent: Jan. 29, 2019

(54) OMEGA-7 FATTY ACID COMPOSITION, METHODS OF CULTIVATION OF TRIBONEMA FOR PRODUCTION OF COMPOSITION AND APPLICATION OF COMPOSITION

(71) Applicant: QINGDAO INSTITUTE OF BIOENERGY AND BIOPROCESS TECHNOLOGY, CHINESE ACADEMY OF SCIENCES, Qingdao, Shandong (CN)

(72) Inventors: Tianzhong Liu, Qingdao (CN); Wenjun Zhou, Qingdao (CN); Hui Wang, Qingdao (CN); Lin Chen, Qingdao (CN)

(73) Assignee: QINGDAO INSTITUTE OF BIOENERGY AND BIOPROCESS TECHNOLOGY, CHINESE ACADEMY OF SCIENCE, Qingdao (CN)

( * ) Notice: Subject to any disclaimer, the term of this patent is extended or adjusted under 35 U.S.C. 154(b) by 0 days.

(21) Appl. No.: 15/535,675

(22) PCT Filed: Nov. 21, 2016

(86) PCT No.: PCT/CN2016/106587
§ 371 (c)(1),
(2) Date: Jun. 13, 2017

(87) PCT Pub. No.: WO2017/166831
PCT Pub. Date: Oct. 5, 2017

(65) Prior Publication Data
US 2018/0042839 A1    Feb. 15, 2018

(30) Foreign Application Priority Data
Apr. 1, 2016 (CN) .......................... 2016 1 0202076

(51) Int. Cl.
| | | |
|---|---|---|
| *A61K 8/9706* | (2017.01) | |
| *A01H 13/00* | (2006.01) | |
| *C11B 1/00* | (2006.01) | |
| *C11B 3/00* | (2006.01) | |
| *C12P 7/64* | (2006.01) | |
| *A23L 33/12* | (2016.01) | |
| *C11B 1/06* | (2006.01) | |
| *C11B 3/16* | (2006.01) | |
| *A01G 33/00* | (2006.01) | |

(52) U.S. Cl.
CPC .......... *A61K 8/9706* (2017.08); *A01H 13/00* (2013.01); *A23L 33/12* (2016.08); *C11B 1/00* (2013.01); *C11B 1/06* (2013.01); *C11B 3/00* (2013.01); *C11B 3/008* (2013.01); *C11B 3/16* (2013.01); *C12P 7/64* (2013.01); *C12P 7/6409* (2013.01); *A01G 33/00* (2013.01)

(58) Field of Classification Search
CPC ................................................... A61K 8/9706
See application file for complete search history.

(56) References Cited

U.S. PATENT DOCUMENTS

2013/0129775 A1   5/2013   Shinde et al.
2014/0275596 A1   9/2014   Astwood et al.

FOREIGN PATENT DOCUMENTS

| CN | 101979498 A | 2/2011 |
| CN | 103960117 A | 8/2014 |
| CN | 105189768 A | 12/2015 |

OTHER PUBLICATIONS

Cao et al., Identification of a Lipokine, a Lipid Hormone Linking Adipose Tissue to Systemic Metabolism, Cell, 2008, 134.
Akazawa Yuko et al., Palmitoleate attenuates palmitate-induced bim and PUMA up-regulation and hepatocyte lipoapoptosis, J. Hepatol, 2010, 52, 586-593.
Misra, Anoop et al., "Obesity, the Metabolic Syndrome, and Type 2 Diabetes in Developing Countries: Role of Dietary Fats and Oils," J. Am Coll Nutr, 2010, 29, 289S-301S.
Rybak, Anastasiya et al., "Acyclic Diene Metathesis with a Monomer from Renewable Resources: Control of Molecular Weight and One-Step Preparation of Block Copolymers," Chem Sus Chem, 2008, 1, 542-547.
Cao, Yujin et al., "Production of free monounsaturated fatty acids by metabolically engineered *Escherichia coli*," Biotechnology for Biofuels, 2014, 7, 59.
Knothe, Gerhard, "Biodesiel Derived from a Model Oil Enriched in Palmitoleic Acid, Macadamia Nut Oil," Energy Fuels 2010, 24(3), 2098-2103.
Yang Baoru et al., "Fatty Acid Composition of Lipids in Sea Buckthorn (*Hippophae rhamnoides* L.), Berries of Different Origins," J. Agric Food Chem, 2001, 49, 1939-1947.
Lang Imke et al., "Fatty acid profiles and their distribution patterns in microalgae: a comprehensive analysis of more than 2000 strains from the SAG culture collection," BMC Plant Biology, 2011, 11, 124.
Beopoulos Athanasios et al., "An overview of lipid metabolism in yeasts and its impact on biotechnological processes," Applied Microbiology and Biotechnology, 2011, 90, 1193-1206.
Liu Yanbin et al., "Bioconversion of crude glycerol to glycolipids in Ustilago maydis," Bioresource Technology, 2011, 102, 3927-3933.
Wang Hui et al., "Integration process of biodesiel production from filamentous oleaginous microalgae Tribonema minus," Bioresource Technology, 2013, 142, 39-44.

(Continued)

*Primary Examiner* — Albert M Navarro
(74) *Attorney, Agent, or Firm* — Oliff PLC (57) ABSTRACT

An omega-7 fatty acid composition from a raw material *Tribonema* sp. obtained under heterotrophy and/or mixotrophy and a method of cultivation of *Tribonema* sp. by way of heterotrophy and/or mixotrophy. The content of omega-7 fatty acid in the omega-7 fatty acid composition is 30% to 70%. The method of cultivation involves nutrient composition of a culture medium, cultivation conditions, and operation steps of a cultivation process. An application of the method in the production of *Tribonema* biomass, lipid rich in omega-7 fatty acid, products with the biomass and/or the lipid as the raw material, etc.

8 Claims, 5 Drawing Sheets

(56) References Cited

OTHER PUBLICATIONS

Guo Fajin et al., "Special biochemical responses to nitrogen deprivation of filamentous oleaginous microalgae *Tribonema* sp.," Bioresource Technology, 2014, 158, 19-24.

Gao Chunfang et al., "Application of sweet sorghum for biodesiel production by heterotrophic microalga Chlorella protothecoides," Applied Energy, 87, 2010, 756-761.

Han Feifei et al., "Enhancement of microalgal biomass and lipid productivities by a model of photoautotrophic culture with heterotrophic cells as seed," Bioresource Technology, 2012, 118, 431-437.

Wang, Hui et al., "Growth and Biochemical Composition of Filamentous Microalgae *Tribonema* sp. as Potential Biofuel Feedstock," Bioprocess Biosyst Eng., vol. 37, 2014, pp. 2607-2613.

Zhou, Wenjun et al., "Advancement of the Researches for Heterotrophic Cultivation of Microalgae," Marine Sciences, vol. 36, No. 2, Dec. 31, 2012 pp. 136-142.

Feb. 13, 2017 International Search Report issued in International Patent Application PCT/CN2016/106587.

Yang, Su-ling et al., "Characteristics of Auto-, Hetero- and Mixotrophic Growth of Chlorella Vulgaris," Journal of Anhui Agricultural Sciences, vol. 41, No. 18, Dec. 31, 2013, pp. 7748-7749 and 7863.

OMEGA-7 FATTY ACID COMPOSITION, METHODS OF CULTIVATION OF TRIBONEMA FOR PRODUCTION OF COMPOSITION AND APPLICATION OF COMPOSITION

TECHNICAL FIELD

The present invention relates to an omega-7 fatty acid composition, methods of cultivation of Tribonema sp. for the production of the composition and application of the composition, and specifically, to a method of cultivating Tribonema sp. by way of heterotrophy and/or mixotrophy, an omega-7 fatty acid composition produced with Tribonema sp. obtained by the method as the raw material, and application of the omega-7 fatty acid composition in the production of food, nutrition, beverages, feeds, chemicals, fuels, cosmetics, skin care products, health products, pharmaceuticals, and food additives, and belongs to the biotechnical field of microalgae.

BACKGROUND ART

Omega-7 fatty acids are monounsaturated fatty acids with a double bond residing at the seventh carbon atom. Palmitoleic acid (C16:1) is one of the omega-7 fatty acids, which is represented by the following chemical formula: $CH_3(CH_2)_5CH=CH(CH_2)_7COOH$. Palmitoleic acid is biosynthesized from palmitic acid by the catalytic action of delta-9 desaturase.

Palmitoleic acid has a significant application value in the fields of medicine, nutrition, industry, etc. For example, palmitoleic acid has been proved to be able to increase the human body's sensitivity to insulin and be effective for diabetes and metabolic syndrome without obvious side effects (Cao H M, et al. Identification of a lipokine, a lipid hormone linking adipose tissue to systemic metabolism. Cell, 2008, 134, 933-944).

Not only that, palmitoleic acid is also able to reduce the level of C-Reactive Protein (CRP), and lower the risks of heart diseases and stroke by reducing inflammations. Moreover, palmitoleic acid may increase the fluidity of the cell membrane, decrease the content of low-density lipoprotein (LDL) cholesterol in blood, and reduce vascular occlusions resulting from the formation of atherosclerotic plaques in blood vessels, thereby preventing arrhythmia and reducing high blood pressure, etc. (Akazawa Y, et al. Palmitoleate attenuates palmitate-induced Bim and PUMA up-regulation and hepatocyte lipoapoptosis. J Hepatol, 2010, 52, 586-593. Misra A, et al. Obesity, the metabolic syndrome, and type 2 diabetes in developing countries: role of dietary fats and oils. J Am Coll Nutr, 2010, 29, S289-S301).

Furthermore, palmitoleic acid has excellent percutaneous permeability, therefore, it also has obvious effects in preventing skin aging and fat deposit, restoring the skin's elasticity, etc., and is an ideal raw material for anti-aging cosmetics.

In addition, palmitoleic acid may be directly used in high-efficiency production of greatly demanded industrial octylene (Rybak A, et al. Acycli diene metathesis with a monomer from renewable resources: control of molecular weight and one-step preparation of block copolymers. Chem Sus Chem, 2008, 1, 542-547). Besides, since palmitoleic acid is a monounsaturated fatty acid and has outstanding characteristics of low-temperature resistance and oxidation resistance, it is fit for producing high-quality biodiesel (Cao Y J, et al. Production of free monounsaturated fatty acids by metabolically engineered Escherichia coli. Biotechnolgy for Biofuels, 2014, 7, 59. Knothe G, et al. Biodiesel derived from a model oil enriched in palmitoleic acid, Macadamia nut oil. Energy Fuel, 2010, 24(3), 2098-2103).

So far, the main raw materials of commercially available palmitoleic acid products at present are wild plants. Many companies choose to extract and separate palmitoleic acid from Hippophae rhamnoides. 25% palmitoleic acid may be accumulated in the pulp of the Hippophae rhamnoides (Yang B, et al. Fatty acid composition of lipids in sea buckthorn (Hippophae rhamnoides L.) berries of different origins. J Agric Food Chem, 2001, 49, 1939-1947). Doxantha unguis-cali and Macadamia integrifolia are also important sources of palmitoleic acid. The content of palmitoleic acid in the seeds of Doxantha unguis-cati is about 60%, and that in the Macadamia integrifolia is about 30%. In addition, mink oil also contains little palmitoleic acid.

However, these wild plants and animals rich in omega-7 fatty acid cannot be planted and commercially produced in large scales like common oil crops due to such reasons as limited resource amount, low yield, narrow geographical distribution or rare population. Main components of seeds of oil crops such as soybean and corn planted in large scales at present include palmitic acid (C16:0), stearic acid (C18:0), oleic acid (C18:1) and linoleic acid (C18:2), and these seeds contain merely trace amount of (less than 2%) palmitoleic acid (Cao Y J, et al. Production of free monounsaturated fatty acids by metabolically engineered Escherichia coli. Biotechnolgy for Biofuels, 2014, 7, 59. Imke L, et al. Fatty acid profiles and their distribution patterns in microalgae: a comprehensive analysis of more than 2000 strains from the SAG culture collection. BMC Plant Biology, 2011, 11, 124), which may not meet the requirements of human beings in eating and industry (Table 1). In recent years, it has been found that fatty acids of some yeasts (e.g., Kluyveromyces polysporus, Torulaspora delbrueckii, and Saccharomyces cerevisiae) include palmitoleic acid in a high ratio. Nevertheless, these yeasts are low in total lipid content, leading to a low ratio of the content of palmitoleic acid in dry cell weight (Beopoulos A, et al. An overview of lipid metabolism in yeasts and its impact on biotechnological processes. Applied Microbiology and Biotechnology, 2011, 90, 1193-1206. Liu Y, et al. Bioconversion of crude glycerol to glycolipids in Ustilago maydis. Bioresource Technology, 2011, 102, 3927-3933).

TABLE 1

Composition of Fatty Acids of Several Typical Oil Crops

| Oil | 14:0 | 16:0 | 16:1 | 18:0 | 18:1 | 18:2 | 18:3 |
|---|---|---|---|---|---|---|---|
| Soybean | NR | 11% | NR | 4.0% | 23.4% | 53.2% | 7.8% |
| Corn | NR | 10.3% | NR | 1.0% | 30.3% | 58.2% | NR |
| Rapeseed | NR | 5.5% | NR | 2.2% | 58.3% | 19.9% | 9.1% |
| Jatropha | NR | 15.3% | 1.3% | 4.1% | 38.4% | 43.4% | NR |
| Palm | 1.0% | 42.8% | NR | 4.5% | 40.5% | 10.1% | 0.2% |

As the advantages of the palmitoleic acid have been increasingly discovered and proved, the demand for the palmitoleic acid will increase significantly. Therefore, seeking for a new resource high in palmitoleic acid content and unrestricted by seasonal and regional factors becomes the first choice to solve the problem of insufficient supply of raw materials.

Tribonema sp. belongs to Tribonema, Tribonemataceae in Heterotrichales under Xanthophyceae in Xanthophyta, and its frond is non-branched filament. Researches show that

*Tribonema* sp. has the characteristics of high growth speed and high lipid content, and the content of palmitoleic acid in its fatty acids profile exceeds 50% (Wang H, et al. Integration process of biodiesel production from filamentous oleaginous microalgae *Tribonema minus*. *Bioresour Technol*, 2013, 142, 39-44. Guo F J, et al. Special biochemical responses to nitrogen deprivation of filamentous oleaginous microalgae *Tribonema* sp. *Bioresour. Technol*. 2014, 158, 19-24.). Therefore, *Tribonema* sp. may become a new raw material for producing the palmitoleic acid instead of the traditional wild plants and animals. Meanwhile, it is imperative to develop a method capable of cultivating *Tribonema* sp. in high density and in large scales.

There are two major ways for large-scale cultivation of microalgae: autotrophy and heterotrophy, wherein by the way of autotrophy, greenhouse gas carbon dioxide can be immobilized and oxygen is released; it is environmentally friendly; however, due to shading effect between the microalgae cells, the utilization of light energy is often greatly restricted. The higher the cell concentration is, the more obvious the shading effect is, which leads to a strong influence on the growth of cells and lipid synthesis. Concerning heterotrophy, the growth of cells relies largely on cells absorbing organic carbon sources; as it is not restricted by light, quick increase of the cell density and high-efficiency lipid synthesis can be achieved by adding organic carbon; however, the protein and pigment contents in heterotrophic algal cells are low when compared with photoautotrophy. Therefore, the above-mentioned two large-scale cultivation modes of microalgae have respective advantages and disadvantages, and should be selected according to specific requirements in practical application.

American patent No. US2013/0129775A1 discloses a composition rich in omega-7 fatty acid and a method of separating omega-7 fatty acid. While this patent sets forth that the composition is derived from algal biomass, the algal type is not specified, and brief description is only made with *Nannochloropsis* as an example.

American patent No. US2014/0275596A1 discloses a blend composition of algal omega-7 and omega-3 fatty acid. While this patent lists multiple algae as sources for producing omega-7 and omega-3 fatty acid blend compositions in detail in its detailed description of the invention, *Tribonema* sp. is not included.

Documents "Application of sweet sorghum for biodiesel production by heterotrophic microalga *Chlorella protothecoides*" (Gao C F, et al. Application of sweet sorghum for biodiesel production by heterotrophic microalga *Chlorella protothecoides*. *Applied Energy*, 2010, 87, 756-761.) and "Enhancement of microalgal biomass and lipid productivities by a model of photoautotrophic culture with heterotrophic cell as seed" (Han F F, et al. Enhancement of microalgal biomass and lipid productivities by a model of photoautotrophic culture with heterotrophic cell as seed. *Bioresour. Technol*, 2012, 118, 431-437) report a method of cultivating microalgae by heterotrophic culture, but the microalgae cultivated by heterotrophic culture is unicellular *Chlorella*. Those skilled in the art should know that the collection process of the *Chlorella* will consume high electric energy or require the addition of a certain quantity of flocculant. *Tribonema* sp., in the filamentous form, can be collected efficiently through simple filtration by bolting silk or air floatation; thus, the cost of collection is reduced, and the addition of flocculant may also be effectively avoided.

Concerning large-scale cultivation of *Tribonema* sp., as the existing researches are all based on photoautotrophy with no research made on heterotrophy or mixotrophy thereof, and the researchers in this art alway focus on heterotrophy of unicellular algae and seldom on multicellular filamentous algae, *Tribonema* sp. is cultivated and industrially used in the mode of autotrophy at present. For example, Chinese patent No. CN103960117A discloses a method for preparing *Tribonema* biological oil, and the *Tribonema* biological oil prepared through the method. In the method disclosed by this patent, a commonly used microalgae culture medium (i.e., BG11 medium) is employed to cultivate *Tribonema* under light to obtain *Tribonema* biomass; the growth pattern of the *Tribonema* sp. is photoautotrophic growth and the *Tribonema* biological oil is also derived from *Tribonema* biomass obtained through photoautotrophic growth; however, restricted by such factors as environment, season, and capacity, and the shading effect between cells, the growth rate of the *Tribonema* sp., the reachable cell density, yield of biomass and yield of lipid of the *Tribonema* need to be further increased.

SUMMARY OF THE INVENTION

In the view of the prior art described above, the present invention provides an effective solution, i.e., cultivating *Tribonema* sp. rich in omega-7 fatty acid in a large scale by way of heterotrophy and/or mixotrophy, and using *Tribonema* cells obtained through this cultivation as the raw material for extraction of an omega-7 fatty acid composition. The content of the omega-7 fatty acid (mostly palmitoleic acid) in the cells is 30% to 70%. By using the method provided by the present invention, *Tribonema* sp. may not be restricted by such factors as environment, season, and capacity during large-scale cultivation, and the reproductive speed of *Tribonema* sp., the yield of biomass and lipid are effectively increased. An important technical means is provided to solve the problems in the large-scale photoautotrophy process of *Tribonema* sp., thereby effectively and rapidly solving the biomass resource problem of the omega-7 fatty acid.

Terminology Note:

Unless otherwise specified, "heterotrophy" in the present invention means cultivation of *Tribonema* sp. without light and in the presence of an organic carbon source, and thus may be interpreted as "fermentation". Specifically, *Tribonema* sp. is kept from light during cultivation, but a culture medium for *Tribonema* sp. should contain appropriate organic carbon source, nitrogen source and phosphate as well as other nutrient substances. Under the heterotrophy condition, *Tribonema* sp. uses the organic carbon source as the energy source and the carbon source for synthesizing biomass. The "mixotrophy" means cultivation of *Tribonema* sp. in the presence of both light and an organic carbon source, and thus may be interpreted as "fermentation under proper light". Specifically, it means providing proper light for the cultivation of *Tribonema* sp., and meanwhile, a culture medium for *Tribonema* sp. should contain an appropriate amount of organic carbon source, nitrogen source and phosphate as well as other nutrient substances. Under the mixotrophy condition, *Tribonema* sp. uses the light energy and/or the organic carbon source as the energy source and uses the organic carbon source and/or carbon dioxide as the carbon source for synthesizing biomass.

In a first aspect of the present invention, provided is a method of cultivation of *Tribonema* sp. The method comprises steps of carrying out heterotrophy and/or mixotrophy of *Tribonema* sp.

In the above-mentioned method of cultivation, the steps of the heterotrophy and/or the mixotrophy include: adding culture medium to a cultivation apparatus, and inoculating the medium with sterile *Tribonema* sp. for cultivation under a cultivation temperature of 2° C. to 40° C., a stirring rate of 1 rpm to 400 rpm, an air bubbling rate of 0.01 vvm to 1 vvm, a pH value of 5 to 10, and a light intensity of 0 μmol photons $m^{-2}$ $s^{-1}$ to 1000 μmol photons $m^{-2}$ $s^{-1}$.

Preferably, the cultivation temperature is 25° C. to 30° C.; the stirring rate is 90 rpm to 270 rpm; the air bubbling rate is 0.1 vvm to 0.2 vvm; the pH value is 7 to 9, and the light intensity is 50 μmol photons $m^{-2}$ $s^{-1}$ to 200 μmol photons $m^{-2}$ $s^{-1}$. Under the preferred cultivation conditions, *Tribonema* sp. may reach higher biomass and lipid content within the same cultivation time.

In the above-mentioned method of cultivation, the culture medium is composed of an organic carbon source, a nitrogen source, a phosphate and other nutrient substances; the concentration of the organic carbon source in the culture medium ranges from 0.1 g/L to 200 g/L, while the concentration of the nitrogen source in the culture medium ranges from 0.1 g/L to 20 g/L, and the concentration of the phosphate in the culture medium ranges from 0.01 g/L to 5 g/L.

Preferably, the concentration of the organic carbon source in the culture medium ranges from 10 g/L to 60 g/L, while the concentration of the nitrogen source in the culture medium ranges from 1 g/L to 4 g/L, and the concentration of the phosphate in the culture medium ranges from 0.05 g/L to 1 g/L.

The organic carbon source is one and/or a mixture in any ratio of glucose, fructose, maltose, sucrose, glyceraldehyde, glycerin, acetates, starch hydrolysis sugar and cellulose hydrolysis sugar.

Preferably, the organic carbon source is glucose.

The nitrogen source is one and/or a mixture in any ratio of yeast extract, peptone, amino acids, cereal pulp, nitrates, urea and ammonium salts.

Preferably, the nitrogen source is peptone.

The other nutrient substances include $MgSO_4$, $CaCl_2$, citric acid, EDTA salts, ferric citrate, carbonates, $ZnSO_4$, $CuSO_4$, $MnCl_2$, $Na_2MoO_4$, $Co(NO_3)_4$, $H_3BO_3$, biotin, vitamin B1 and vitamin B12.

In the above-mentioned method, the cultivation apparatus should be an enclosed or semi-enclosed apparatus capable of accommodating liquid-state and/or solid-state medium(s) and maintaining the sterile growth of *Tribonema* sp. The cultivation apparatus includes but is not limited to: mechanical stirring ventilating fermentation tank, self-suction fermentation tank, airlift fermentation tank and tower fermentation tank.

In the above-mentioned method of cultivation, the sterile *Tribonema* sp. strain is obtained by way of: adding an appropriate amount of antibiotic to the *Tribonema* suspension, transferring *Tribonema* sp. to sterile water and resuspending it after 2 days, and checking whether the resuspension solution is sterile or not by a commonly known technical means in the biotechnical field, and repeating this step until the sterile *Tribonema* sp. strain is obtained.

The appropriate amount of antibiotic means a working solution of chloramphenicol, kanamycin, streptomycin, penbritin or other antibiotics with a concentration of 20 mg/L to 200 mg/L.

In the above-mentioned method of cultivation, the method of heterotrophy and/or mixotrophy of *Tribonema* sp. may also be popularly referred to as fermentation cultivation of *Tribonema* sp. The fermentation cultivation modes of *Tribonema* sp. may be batch fermentation and/or continuous (feeding) fermentation and/or fed-batch fermentation.

In some embodiments of the present invention, *Tribonema* sp. is cultivated in the modes of batch fermentation and fed-batch fermentation, and the biomass may be 28 g/L and 30 g/L, respectively, after 6 days.

In the present invention, *Tribonema* sp. is more than twenty strains of *Tribonema*, including but not limited to *Tribonema aequale*, *Tribonema affine*, *Tribonema elegans*, *Tribonema gayanum*, *Tribonema intermixtum*, *Tribonema minus*, *Tribonema monochloron*, *Triconema angustlissimum*, *Tribonema pyrenigerum*, *Tribonema regulare*, *Tribonema siderophilum*, *Tribonema spirotaenia*, *Tribonema ulotrichoides*, *Tribonema utriculosum*, *Tribonema viride*, *Tribonema vulgare*, *Tibonema yamadanum*, *Tribonema bombycinum* and *Tribonema vermichloris*.

Preferably, the *Tribonema* sp. in the present invention is *Tribonema aequale*, *Tribonema vulgare*, *Tribonema minus*, *Tribonema ulotrichoides* and *Tribonema utriculosum*.

In the above-mentioned method of cultivation, the cultivated *Tribonema* sp. is one or a combination of two or more of the above-mentioned *Tribonema* strains.

In a second aspect of the present invention, provided is a method of production of an omega-7 fatty acid composition. The method of production comprises a step of carrying out heterotrophy and/or mixotrophy of *Tribonema* sp., a step of collecting a *Tribonema* cultivation suspension to obtain *Tribonema* biomass, and a step of obtaining an omega-7 fatty acid composition through extraction and/or squeezing treatment.

In the above-mentioned method of production, the *Tribonema* cultivation suspension is collected by a commonly known technical means, such as centrifuging, filtration, air flotation, and the like, to obtain the *Tribonema* biomass.

In the above-mentioned method of production, after the *Tribonema* biomass is obtained, it is treated by a commonly known extraction method in the art, such as chloroform-methanol extraction, normal hexane extraction, supercritical carbon dioxide extraction, and the like, or a squeezing method, such as hot squeezing, cold squeezing, and the like, thereby obtaining *Tribonema* lipid and the omega-7 fatty acid composition.

In a third aspect of the present invention, provided is an omega-7 fatty acid composition, in which the content of omega-7 fatty acid is 30% to 70%, and the content of palmitoleic acid is 30% to 70%. The omega-7 fatty acid composition disclosed above may be used to produce products in the fields including but not limited to: food, nutrition, beverages, feeds, chemicals, fuels, cosmetics, skin care products, health products, pharmaceuticals, and food additives.

The *Tribonema* biomass obtained by the method of cultivation provided in the present invention, not extracted or squeezed, may also be used to produce products in the fields including but not limited to: food, nutrition, beverages, feeds, chemicals, fuels, cosmetics, skin care products, health products, pharmaceuticals, and food additives.

Concerning the omega-7 fatty acid and/or the *Tribonema* biomass obtained by use of the methods provided by the present invention, as widely known in the fields of food and medicine, the omega-7 fatty acid has been proved to be able to increase the human body's sensitivity to insulin and be effective for diabetes and metabolic syndrome without obvious side effects, and therefore, the omega-7 fatty acid composition, the method of cultivation of *Tribonema* sp. and the product rich in palmitoleic acid disclosed by the present invention can be applied to the field of pharmaceuticals. Those skilled in the technical art should know that the omega-7 fatty acid is able to reduce the level of C-Reactive Protein (CRP), and lower the risks of heart diseases and stroke by reducing inflammations. Moreover, the omega-7 fatty acid may increase the fluidity of the cell membrane, decrease the content of low-density lipoprotein (LDL) cholesterol in blood, and reduce vascular occlusions resulting from the formation of atherosclerotic plaques in blood vessels, thereby preventing arrhythmia and reducing high blood pressure, etc. Therefore, the omega-7 fatty acid composition, the method of cultivation of *Tribonema* sp. and the product rich in palmitoleic acid disclosed by the present invention can be applied to the fields of nutrition and health products.

Those skilled in the art should also know that the omega-7 fatty acid has excellent percutaneous permeability, and therefore, it also has obvious effects in preventing skin aging and fat deposit, restoring the skin's elasticity, etc., and is an ideal raw material for anti-aging cosmetics. Therefore, the omega-7 fatty acid composition, the method of cultivation of *Tribonema* sp. and the product rich in palmitoleic acid disclosed by the present invention can be applied to the fields of cosmetics and skin care products.

Beside, microalgae have been widely applied to the fields of food, beverages, feeds, and food additives. *Tribonema* sp., as one type of microalgae, may also be applied to the above-mentioned related fields.

As another application of the present invention, the palmitoleic acid may be directly used in high-efficiency production of greatly demanded industrial octylene. Besides, since the palmitoleic acid is a monounsaturated fatty acid and has outstanding characteristics of low-temperature resistance and oxidation resistance, it is fit for producing high-quality biodiesel. Therefore, the omega-7 fatty acid composition (with palmitoleic acid as the main component), the method of cultivation of *Tribonema* sp. and the product rich in palmitoleic acid disclosed by the present invention can be applied to the fields of chemicals and fuels.

In a fourth aspect of the present invention, provided is a product, which is produced by the method of cultivation of *Tribonema* sp. disclosed by the present invention, or derived from the *Tribonema* biomass and/or the *Tribonema* lipid and/or the omega-7 fatty acid composition obtained by the method of cultivation disclosed by the present invention.

The products may be products in the fields including but not limited to: food, nutrition, beverages, feeds, chemicals, fuels, cosmetics, skin care products, health products, pharmaceuticals, and/or food additives.

The present invention has the following beneficial effects:

The traditional raw materials for omega-7 fatty acid are mainly wild plants and animals, and due to the reason of small seeds, low yield, narrow geographical distribution or rare population, it leads to heavy insufficiency of raw materials for omega-7 fatty acid. According to the present invention, *Tribonema* sp. rich in omega-7 fatty acid is chosen as the new raw material for producing the omega-7 fatty acid, and a method of cultivation that may effectively increase the reproductive speed, biomass yield and lipid yield of *Tribonema* sp. is provided; it is avoided that the *Tribonema* sp. is restricted by such factors as environment, season, and capacity in large-scale cultivation, and the current situation of insufficient raw materials for the omega-7 fatty acid is effectively solved.

DETAILED DESCRIPTION OF THE EMBODIMENTS

The present invention will be further described in conjunction with embodiments. It should be noted that the following descriptions are merely intended to explain the present invention, rather than limiting the contents thereof.

*Tribonema* species used in the present invention are all recorded wild species, which may be commercially available for those of ordinary skill or may be separated and purified from natural water, and may not be subject to deposit of biological materials for the patent procedure.

Embodiment 1

A method of heterotrophy and/ormixotrophy of *Tribonema* sp. comprises the following specific steps:

(1) An appropriate amount of antibiotic is added to the suspension of *Tribonema* sp. by a commonly known technical means in the biotechnical field, and the *Tribonema* sp. is transferred into sterile water and resuspended after 2 days. A commonly known detection means in the biotechnical field is used to check whether the resuspension solution is sterile or not. This step is repeated until a sterile *Tribonema* strain is obtained. The appropriate amount of antibiotic means a working solution of chloramphenicol, kanamycin, streptomycin, penbritin or other antibiotics that has a concentration of 20 mg/L to 200 mg/L.

(2) A culture medium containing an organic carbon source, a nitrogen source, a phosphate and other nutrient substances is put into a cultivation apparatus, and sterilized for 20 minutes at 115° C.

(3) After the temperature of the culture medium in step (2) drops to a room temperature, the sterile *Tribonema* strain obtained in step (1) is inoculated into the cultivation apparatus for heterotrophy and/or mixotrophy, wherein the conditions of the heterotrophy include: the glucose concentration in the culture medium is 10 g/L and no light is offered; the conditions of the mixotrophy include: the glucose concentration in the culture medium is 10 g/L and light of 50 µmol photons $m^{-2}$ $s^{-1}$ is offered; the cultivation temperature is 25° C., and the revolving speed of the shaker is 180 rpm.

(4) After completion of the cultivation, *Tribonema* cultivation suspension is collected by a commonly known technical means in the biotechnical field, such as filtration, air flotation, and the like, thereby obtaining *Tribonema* biomass.

After the *Tribonema* biomass is obtained, the obtained biomass is treated by means of a commonly known extraction method in the art, such as chloroform-methanol extraction, normal hexane extraction, and the like, or a squeezing method, such as hot squeezing, cold squeezing, and the like, thereby obtaining *Tribonema* lipid and omega-7 fatty acid composition.

Under the conditions of heterotrophy and mixotrophy, the composition of fatty acids of *Tribonema* sp. are shown in Table 2 below. Under the condition of heterotrophy, the total lipid content of the *Tribonema* sp. is 40.3% of dry biomass, wherein the content of omega-7 fatty acid is 58.4% of total fatty acids; that is, the content of palmitoleic acid is 58.4% of total fatty acids. Under the condition of mixotrophy, the total lipid content of the *Tribonema* sp. is 43.5% of dry biomass, wherein the content of omega-7 fatty acid is 50.1% of total fatty acids; that is, the content of palmitoleic acid is 50.1% of total fatty acids.

TABLE 2

Composition of Fatty Acids of *Tribonema* sp. Under the Conditions of Heterotrophy and Mixotrophy

| Oil | 14:0 | 16:0 | 16:1 | 18:0 | 18:1 | 18:2 | 20:4 | 20:5 | others |
|---|---|---|---|---|---|---|---|---|---|
| Heterotrophy | 4.6% | 19.1% | 58.4% | 0.7% | 2.7% | 1.5% | 4.3% | 5.1% | 3.6% |
| Mixotrophy | 8.7% | 28.0% | 50.1% | 1.7% | 3.4% | 0.3% | 2.4% | 2.8% | 2.6% |

Embodiment 2

Growth, lipid content and composition of fatty acids of *Tribonema* sp. under the conditions of heterotrophy, mixotrophy, and photoautotrophy

*Tribonema* sp. is cultivated separately under the conditions of heterotrophy, mixotrophy, and photoautotrophy. The conditions of heterotrophy include: the glucose concentration is 10 g/L, the peptone concentration is 2 g/L, and reference for other nutrient concentrations is made according to BG11 culture medium; the light intensity is 0 µmol photons $m^{-2}$ $s^{-1}$, and the initial biomass is 0.3 g/L. The conditions of mixotrophy include: the glucose concentration is 10 g/L, while the peptone concentration is 2 g/L, and reference for other nutrient concentrations is made according to the BG11 culture medium; the light intensity is 50 µmol photons $m^{-2}$ $s^{-1}$, and the initial biomass is 0.3 g/L. The conditions of photoautotrophy include: the glucose concentration is 0 g/L, while the peptone concentration is 0 g/L, and reference for other nutrient concentrations is made according to the BG11 culture medium; the light intensity is 50 µmol photons $m^{-2}$ $s^{-1}$, and the initial biomass is 0.3 g/L. Nutrient components of the BG11 culture medium are shown in Table 3 below. 250 mL triangular flasks are used as the cultivation containers, and a single volume of cultivation is 100 mL. The triangular flasks are placed in the shaker for shaking cultivation. The temperature and the revolving speed of the shaker are set to 25° C. and 180 rpm, respectively. In the cultivation process, samples are taken every day at regular time for determination of biomass (dry weight). After completion of the cultivation, the *Tribonema* biomass is collected and freeze-dried; next, *Tribonema* lipid is extracted therefrom by using a chloroform-methanol solution, and the composition of fatty acids thereof is analyzed by gas chromatography.

TABLE 3

Composition and Concentration of Nutrient in BG11 Cultivation Solution

| Type of Nutrient | | Concentration (m g/L) |
|---|---|---|
| Sodium nitrate | $NaNO_3$ | 1500 |
| Hydrogen phosphate | $K_2HPO_4$ | 40 |
| Magnesium sulfate | $MgSO_4 \cdot 7H_2O$ | 75 |
| Calcium chloride | $CaCl_2 \cdot 2H_2O$ | 36 |
| Citric acid | Citric acid | 6 |
| Ammonium ferric citrate | Ammonium ferric citrate | 6 |
| Disodium ethylene diamine tetraacetate | $EDTANa_2$ | 1 |
| Sodium carbonate | $Na_2CO_3$ | 20 |
| Boric acid | $H_3BO_3$ | 2.86 |
| Magnesium chloride | $MnCl_2 \cdot 4H_2O$ | 1.81 |
| Zinc sulfate | $ZnSO_4 \cdot 7H_2O$ | 0.22 |
| Sodium molybdate | $Na_2MoO_4 \cdot 2H_2O$ | 0.39 |

TABLE 3-continued

Composition and Concentration of Nutrient in BG11 Cultivation Solution

| Type of Nutrient | | Concentration (m g/L) |
|---|---|---|
| Copper sulfate | $CuSO_4 \cdot 5H_2O$ | 0.08 |
| Cobalt nitrate | $Co(NO_3)_2 \cdot 6H_2O$ | 0.05 |

Figure 1:
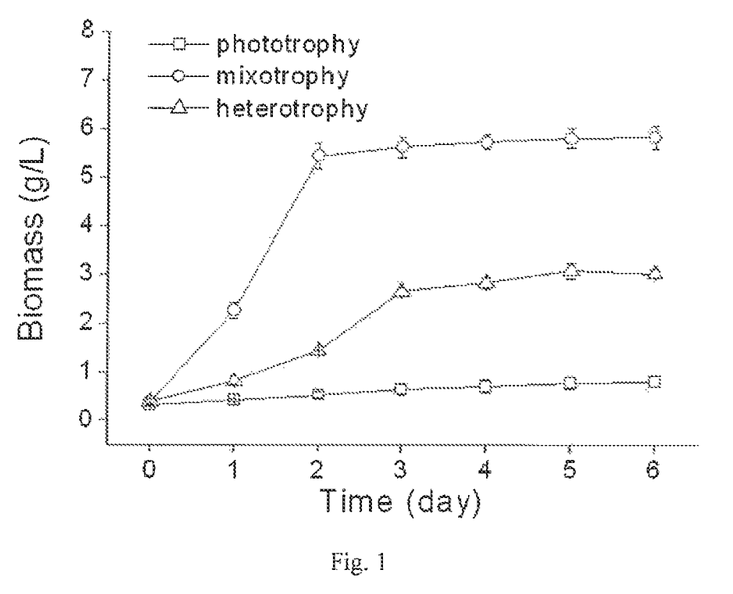
FIG. 1 shows comparison of growth of *Tribonema* sp. under the conditions of heterotrophy, mixotrophy and photoautotrophy.

As shown in FIG. 1, in three different cultivation modes, *Tribonema* sp. grows fastest under mixotrophy with the highest reachable maximum biomass, wherein the biomass may be 5.5 g/L after 2 days. Under the condition of heterotrophy, the growth speed of *Tribonema* sp. is slightly slowed down, and the reachable maximum biomass thereof is also reduced, wherein the biomass may be about 2.7 g/L after 3 days. Under the condition of photoautotrophy, the growth speed of *Tribonema* sp. is greatly slowed down, and the biomass reachable at completion of the cultivation is only 0.8 g/L, which is far lower than that in the other two cultivation modes. It thus can be seen that the method of heterotrophy and mixotrophy of *Tribonema* sp. provided by the present invention may allow *Tribonema* sp. to obtain higher biomass within shorter time.

Figure 2:
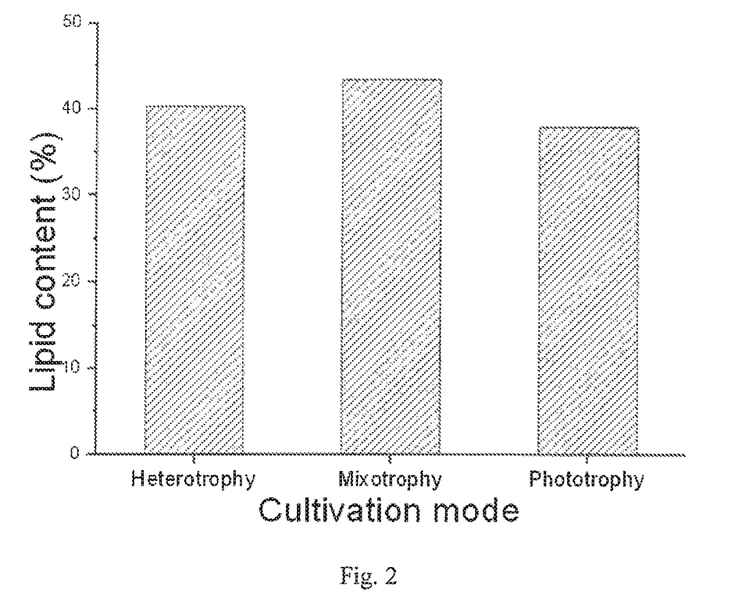
FIG. 2 shows comparison of lipid content of *Tribonema* sp. under the conditions of heterotrophy, mixotrophy and photoautotrophy.

As shown in FIG. 2, in three different cultivation modes, the lipid content of *Tribonema* sp. is the highest under mixotrophy, the second under heterotrophy, and the lowest under heterotrophy with just tiny differences thereamong, and the lipid content is maintained at about 40% in all the three modes. It thus can be seen that the method of heterotrophy and mixotrophy of *Tribonema* sp. provided by the present invention maintains the characteristic of high lipid content of *Tribonema* sp. while increasing the growth speed and biomass thereof.

Figure 3:
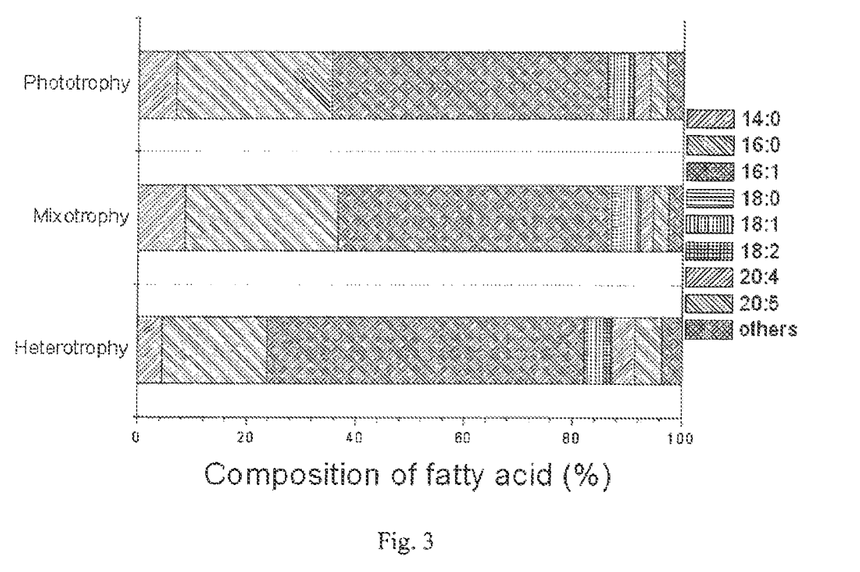
FIG. 3 shows comparison of composition of fatty acids of *Tribonema* sp. under the conditions of heterotrophy, mixotrophy and photoautotrophy.

FIG. 3 shows the composition of fatty acids of *Tribonema* sp. in three different cultivation modes. In all the three cultivation modes, the composition of fatty acids of *Tribonema* sp. mainly includes C16:0 and C16:1 (i.e., palmitoleic acid), and the content of the two fatty acids is about 80% of the total fatty acids, wherein the content of C16:1 is the highest, accounting for about 50% to 60% of the total fatty acids. It needs to be noted that under the two conditions of mixotrophy and photoautotrophy, the composition of fatty acids of *Tribonema* sp. is substantially identical, but under the condition of heterotrophy, the composition of fatty acids of *Tribonema* sp. differs from that under the two former conditions to a certain extent as follows: a decrease of the content of C16:0 from 28% to 19%, and an increase of the content of C16:1 from 50% to 58%.

Embodiment 3

Influence of different organic carbon sources on the growth of *Tribonema* sp.

Under the condition of mixotrophy, glucose, glycerin, and sodium acetate are separately used as the organic carbon source to cultivate *Tribonema* sp. The conditions of mixotrophy include: the concentration of the organic carbon source is 10 g/L, while the peptone concentration is 2 g/L, and reference for other nutrient concentrations is made according to the BG11 culture medium; the light intensity is 50 µmol photons $m^{-2} s^{-1}$, and the initial biomass is 0.3 g/L. 250 mL triangular flasks are used as the cultivation containers, and a single volume of cultivation is 100 mL. The triangular flasks are placed in the shaker for shaking cultivation. The temperature and the revolving speed of the shaker are set to 25° C. and 180 rpm, respectively. In the cultivation process, samples are taken every day at regular time for determination of biomass (dry weight).

Figure 4:
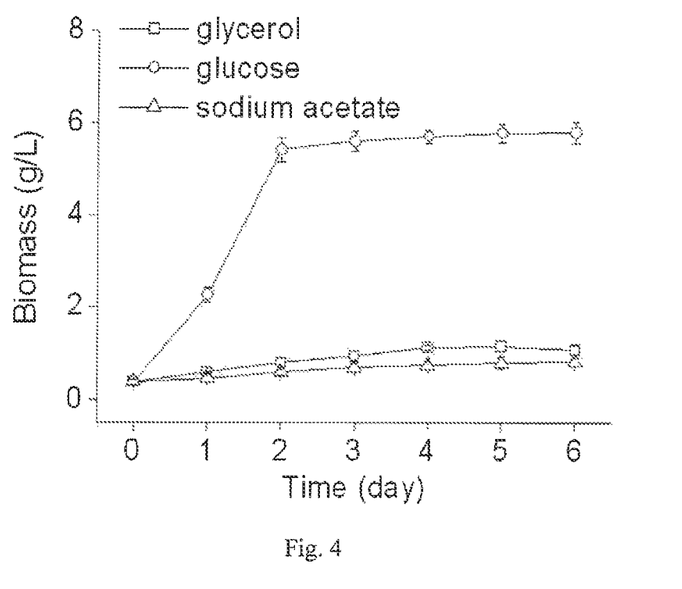
FIG. 4 shows growing states of *Tribonema* sp. under different organic carbon source conditions.

As shown in FIG. 4, among the three selected organic carbon sources in this embodiment, the glucose produces the best effect. *Tribonema* sp. can grow fast with the glucose, and the biomass thereof may be 5.5 g/L after 2 days. Glycerin and sodium acetate may also be used as the organic carbon source for the growth of *Tribonema* sp., but *Tribonema* sp. grows more slowly with the two organic carbon sources.

Embodiment 4

Influence of initial glucose concentration on the growth of *Tribonema* sp.

Under the condition of mixotrophy, the glucose is used as the organic carbon source to cultivate *Tribonema* sp. The conditions of mixotrophy include: the glucose concentration is 5 g/L to 60 g/L, while the peptone concentration is 2 g/L, and reference for other nutrient concentrations is made according to the BG11 culture medium; the light intensity is 50 µmol photons $m^{-2} s^{-1}$, and the initial biomass is 0.3 g/L. 250 mL triangular flasks are used as the cultivation containers, and a single volume of cultivation is 100 mL. The triangular flasks are placed in the shaker for shaking cultivation. The temperature and the revolving speed of the shaker are set to 25° C. and 180 rpm, respectively. In the cultivation process, samples are taken every day at regular time for determination of biomass (dry weight).

Figure 5:
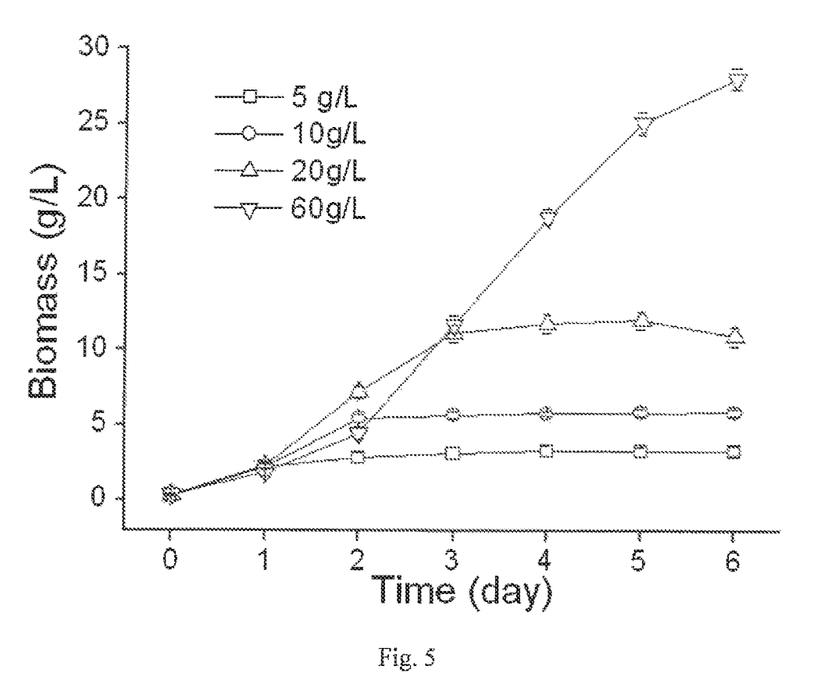
FIG. 5 shows growing states of *Tribonema* sp. under different initial glucose concentration conditions.

As shown in FIG. 5, with the increase of the initial glucose concentration, the reachable maximum biomass of *Tribonema* sp. also increases gradually. When the initial glucose concentration is 5 g/L, the reachable maximum biomass is about 3 g/L; and when the initial glucose concentration is increased to 60 g/L, the reachable maximum biomass is about 28 g/L. With the increase of the initial glucose concentration, the cultivation time required to reach the maximum biomass also increases gradually. It needs to be noted that when the initial glucose concentration is high, the growth of *Tribonema* sp. is inhibited to a certain extent within the first 1 to 2 days of cultivation, during which period *Tribonema* sp. grows relatively slowly; however, this inhibition effect is no longer obvious with the cultivation time going, and the biomass of *Tribonema* sp. may increase rapidly.

Embodiment 5

Influence of stirring rate on the growth of *Tribonema* sp.

Under the condition of mixotrophy, glucose is used as the organic carbon source to cultivate *Tribonema* sp. The conditions of mixotrophy include: the glucose concentration is 10 g/L, while the peptone concentration is 2 g/L, and reference for other nutrient concentrations is made according to the BG11 culture medium; the light intensity is 50 µmol photons $m^{-2} s^{-1}$, and the initial biomass is 0.3 g/L. 250 mL triangular flasks are used as the cultivation containers, and a single volume of cultivation is 100 mL. The triangular flasks are placed in the shaker for shaking cultivation at a temperature set to 25° C. and a stirring rate set to a range of 90 to 270 rpm. In the cultivation process, samples are taken every day at regular time for determination of biomass (dry weight).

Figure 6:
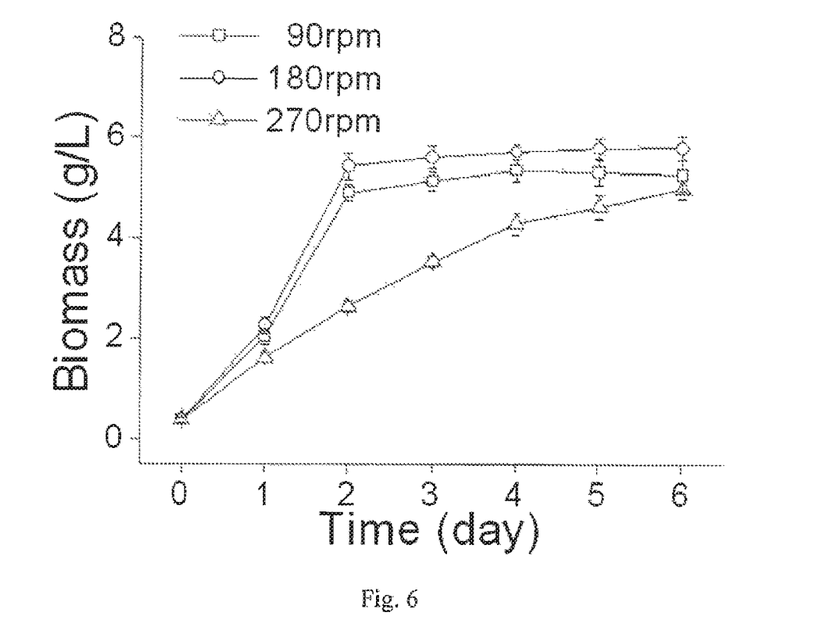
FIG. 6 shows growing states of *Tribonema* sp. under different stirring rate conditions.

As shown in FIG. 6, when the stirring rate is 90 rpm and 180 rpm, *Tribonema* sp. grows fast, and may reach a stationary phase after 2 days, and there is a small difference in the reachable maximum biomass between the two. When the stirring rate is 270 rpm, *Tribonema* sp. grows in a slower way obviously with biomass continuously increasing in the whole cultivation process until reaching about 5 g/L. This result indicates that a relatively mild stirring environment is more advantageous for the growth of *Tribonema* sp.

Embodiment 6

Influence of initial inoculum dose on the growth of *Tribonema* sp.

Under the condition of mixotrophy, glucose is used as the organic carbon source to cultivate *Tribonema* sp. The conditions of mixotrophy include: the glucose concentration is 10 g/L, while the peptone concentration is 2 g/L, and reference for other nutrient concentrations is made according to the BG11 culture medium; the light intensity is 50 µmol photons $m^{-2} s^{-1}$; the cultivation temperature is 25° C.; and the initial inoculum dose is 0.1 to 3 g/L. 1500 mL column airlift reactors are used as the cultivation apparatus, and a single volume of cultivation is 1000 mL. Filtered air is bubbled into the column airlift reactors at a rate of 0.1 vvm. In the cultivation process, samples are taken every day at regular time for determination of biomass (dry weight).

Figure 7:
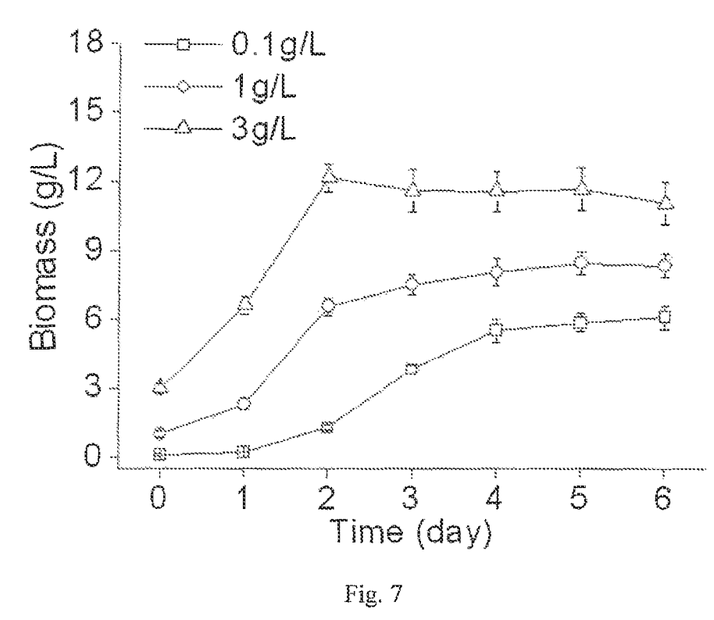
FIG. 7 shows growing states of *Tribonema* sp. under different initial inoculum dose conditions.

Results are shown in FIG. 7, with the increase of the initial inoculum dose, the reachable maximum biomass of *Tribonema* sp. is increased significantly, and the cultivation time required to reach the maximum biomass is also shortened obviously.

Embodiment 7

Batch fermentation cultivation of *Tribonema* sp.

Under the condition of mixotrophy, glucose is used as the organic carbon source to cultivate *Tribonema* sp. by way of batch fermentation. The conditions of mixotrophy include: the glucose concentration is 60 g/L, while the peptone concentration is 12 g/L, and the phosphate concentration is 0.4 g/L, with reference for other nutrient concentrations being made to the BG1 culture medium; and the initial inoculum dose is 0.3 g/L. A 10 L light-transmitting fermentation tank is used as the cultivation apparatus, and the volume of cultivation is 8 L. An external LED lamp is used as the light source with the light intensity of 50 µmol photons $m^{-2}$ $s^{-1}$. Filtered air is bubbled into the fermentation tank at a rate of 0.1 vvm. The cultivation temperature and the stirring rate are set to 25° C. and 180 rpm, respectively. In the cultivation process, samples are taken every day at regular time for determination of biomass (dry weight) and determination of the residual volume of glucose in the culture medium. The determination of the residual volume of glucose in the culture medium is performed by a biosensor.

Figure 8:
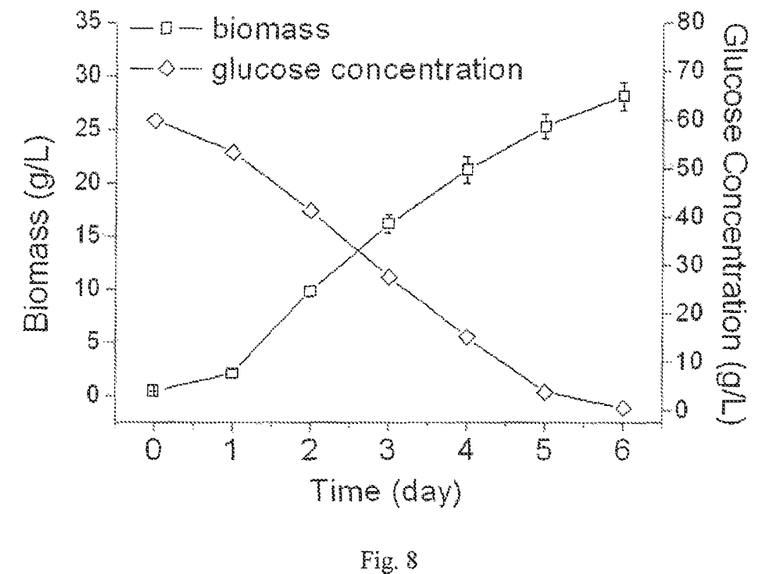
FIG. 8 shows a growth curve of *Tribonema* sp. and a glucose concentration variation curve in a batch fermentation mode.

FIG. 8 shows a growth curve of *Tribonema* sp. and a glucose concentration variation curve in a culture medium under the batch fermentation mode. As can be seen in the figure, in the first day of cultivation, the growth of *Tribonema* sp. is inhibited to a certain extent, and then *Tribonema* sp. begins growing fast with the content of glucose in the cultivation solution decreasing fast correspondingly. At day 6 of cultivation, the content of glucose in the culture medium decrease to 0, and the biomass of the *Tribonema* sp. may be 28 g/L.

Embodiment 8

Fed-batch fermentation cultivation of *Tribonema* sp.

Under the condition of mixotrophy, glucose is used as the organic carbon source to cultivate *Tribonema* sp. by way of fed-batch fermentation. The conditions of mixotrophy include: the glucose concentration is 10 g/L, while the peptone concentration is 2 g/L, and the phosphate concentration is 0.4 g/L, with reference for other nutrient concentrations being made to the BG11 culture medium; and the initial inoculum dose is 0.3 g/L, wherein supplementation of glucose by 10 g/L and peptone by 2 g/L are made to the culture medium every day. A 10 L light-transmitting fermentation tank is used as the cultivation apparatus, and the volume of cultivation is 8 L. An external LED lamp is used as the light source with the light intensity of 50 µmol photons $m^{-2}$ $s^{-1}$. Filtered air is bubbled into the fermentation tank at a rate of 0.1 vvm. The cultivation temperature and the stirring rate are set to 25° C. and 180 rpm, respectively. In the cultivation process, samples are taken every day at regular time for determination of biomass (dry weight) and determination of the residual volume of glucose in the culture medium. The determination of the residual volume of glucose in the culture medium is performed by a biosensor. It needs to be noted that the sampling process every day should be carried out before the supplementation of glucose and peptone.

Figure 9:
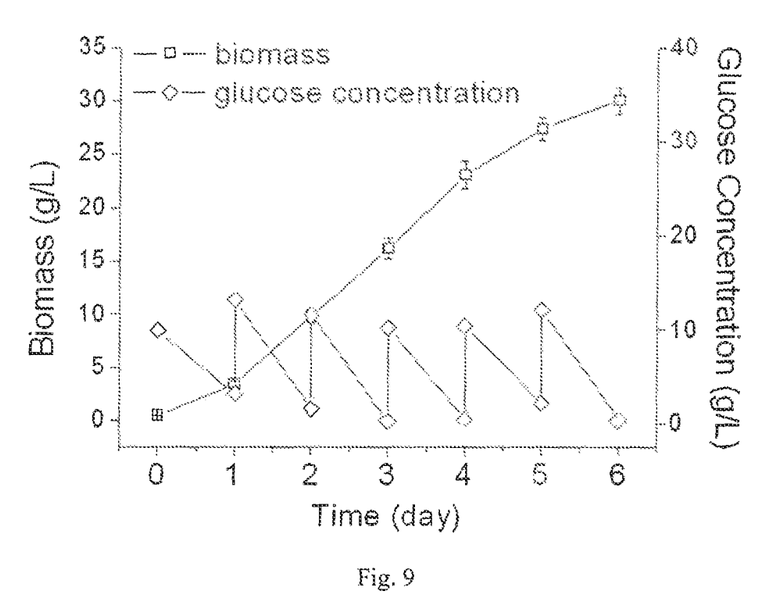
FIG. 9 shows a growth curve of *Tribonema* sp. and a glucose concentration variation curve in a fed-batch fermentation mode.

FIG. 9 shows a growth curve of *Tribonema* sp. and a glucose concentration variation curve in a culture medium in the fed-batch fermentation mode. As can be seen in the figure, since the beginning of cultivation, *Tribonema* sp. may keep growing fast until the completion of cultivation. Correspondingly, the glucose supplemented every day may be almost completely absorbed and utilized by the glucose before next supplementation in the next day. The biomass of *Tribonema* sp. may be 30 g/L after 6 days of fed-batch fermentation cultivation with the yield of biomass being 5 g/L/d. After the completion of cultivation, the *Tribonema* biomass is collected and freeze-dried, and then *Tribonema* lipid is extracted therefrom by using a chloroform-methanol solution; the result of measurement indicates that the lipid content of *Tribonema* sp. may be 45% of dry weight of the biomass with the yield of the lipid being 2.25 g/L/d. The composition of fatty acids thereof is analyzed by gas chromatography, and the result shows that the content of omega-7 fatty acid may be 50% of the total fatty acids with the yield of omega-7 fatty acid being 1.125 g/L/d. As the omega-7 fatty acid is palmitoleic acid in *Tribonema* sp., it means that the content of the palmitoleic acid is 50% of the total fatty acid with the yield of the palmitoleic acid being 1.125 g/L/d.

The invention claimed is:

1. A method of cultivation of Tribonema sp., comprising the steps to carry out heterotrophy and/or mixotrophy of *Tribonema* sp.

2. The method of cultivation of claim 1, wherein the heterotrophy and/or the mixotrophy of the *Tribonema* strain are/is implemented in a batch fermentation mode and/or a continuous fermentation mode and/or a fed-batch fermentation mode.

3. The method of cultivation of claim 1, wherein the *Tribonema* sp. is one or a combination of two or more selected from *Tribonema aequale, Tribonema affine, Tribonema elegans, Tribonema gayanum, Tribonema intermixtum, Tribonema minus, Tribonema monochloron, Triconema angustissimum, Tribonema pyrenigerum, Tribonema regulare, Tribonema siderophilum, Tribonema spirotaenia, Tribonema ulotrichoides, Tribonema utriculosum, Tribonema viride, Tribonema vulgare, Tribonema yamadanum, Tribonema bombycinum* and *Tribonema vermichloris*.

4. The method of cultivation of claim 1, wherein the steps of the heterotrophy and/or the mixotrophy comprise adding a culture medium to a cultivation apparatus, and inoculating the culture medium with a sterile *Tribonema* strain for cultivation under a cultivation temperature of 2° C. to 40° C., a stirring rate of 1 rpm to 400 rpm, an air bubbling rate of 0.01 vvm to 1 vvm, a pH value of 5 to 10, and a light intensity of 0 µmol photons $m^{-2}$ $s^{-1}$ to 1000 µmol photons $m^{-2}$ $s^{-1}$.

5. The method of cultivation of claim 4, wherein the culture medium is comprised of an organic carbon source, a nitrogen source, a phosphate and other nutrient substances; a concentration of the organic carbon source in the culture medium ranges from 0.1 g/L to 200 g/L, while a concentration of the nitrogen source in the culture medium ranges from 0.1 g/L to 20 g/L, and a concentration of the phosphate in the culture medium ranges from 0.01 g/L to 5 g/L.

6. The method of cultivation of claim 5, wherein the organic carbon source is one and/or a mixture in any ratio of glucose, fructose, maltose, sucrose, glyceraldehyde, glycerin, acetates, starch hydrolysis sugar and cellulose hydrolysis sugar;

the nitrogen source is one and/or a mixture in any ratio of yeast extract, peptone, amino acids, cereal slurry, nitrates, urea and ammonium salts; and the other nutrient substances comprise $MgSO_4$, $CaCl_2$, citric acid, EDTA salts, ferric citrate, carbonates, $ZnSO_4$, $CuSO_4$, $MnCl_2$, $Na_2MoO_4$, $Co(NO_3)_4$, $H_3BO_3$, biotin, vitamin B1 and vitamin B12.

7. The method of cultivation of claim 4, wherein the cultivation apparatus is an enclosed or semi-enclosed apparatus capable of accommodating liquid-state and/or solid-state medium(s) and maintaining sterile growth of *Tribonema* sp.

8. A method of production of an omega-7 fatty acid composition, comprising: the step of carrying out heterotrophy and/or mixotrophy of *Tribonema* sp. in claim 1, and a step of collecting a *Tribonema* cultivation suspension to obtain *Tribonema* biomass, and a step of obtaining an omega-7 fatty acid composition through extraction and/or squeezing treatment.

* * * * *